United States Patent [19]

Bookwalter et al.

[11] 4,424,724
[45] Jan. 10, 1984

[54] MULTI-POSITION RATCHET MECHANISM

[75] Inventors: John R. Bookwalter, Brattleboro, Vt.; Alan I. West, Concord, Mass.

[73] Assignee: Codman & Shurtleff, Inc., Randolph, Mass.

[21] Appl. No.: 309,951

[22] Filed: Oct. 9, 1981

[51] Int. Cl.³ .............................................. G05G 5/06
[52] U.S. Cl. ....................................... 74/540; 128/20
[58] Field of Search ...................... 128/3, 12, 20, 275, 128/303 B; 74/540, 575, 577 C, 577 M, 578, 534; 269/68, 212, 214, 215, 322, 325, 326

[56] References Cited

U.S. PATENT DOCUMENTS

| | | | |
|---|---|---|---|
| 677,181 | 6/1901 | Dardano | 269/326 |
| 1,433,153 | 10/1922 | Robinson | 269/215 |
| 3,196,875 | 7/1965 | Pfeiffer | 128/303 B |
| 3,550,584 | 12/1970 | Ring | 128/12 |
| 3,965,890 | 6/1976 | Gauthier | 128/20 |
| 4,254,763 | 3/1981 | McCready et al. | 128/20 |
| 4,267,748 | 5/1981 | Grunewald et al. | 74/578 |
| 4,337,761 | 7/1982 | Upsher | 128/11 |

Primary Examiner—Kyle L. Howell
Assistant Examiner—Max F. Hindenburg
Attorney, Agent, or Firm—Donal B. Tobin

[57] ABSTRACT

A multi-position ratchet mechanism for holding a surgical retractor blade which permits a retractor blade to be rotated into the wound and retracted at the same time to duplicate the natural "toe-in" method of retraction achieved with the hand. The ratchet mechanism includes a ratchet holder to which is pivotably attached a ratchet pivot housing. The retractor blade is mounted in an opening projecting through ratchet pivot housing and held in position by a retractor pawl attached to the ratchet pivot housing. The ratchet pivot housing also has a curved ratchet which depends into a cooperating slot in the ratchet holder and engages a pivot pawl rotatably mounted and spring biased into the ratchet slot. The holder includes a transverse slot which slides onto an oval ring which is mounted about the incision site.

5 Claims, 4 Drawing Figures

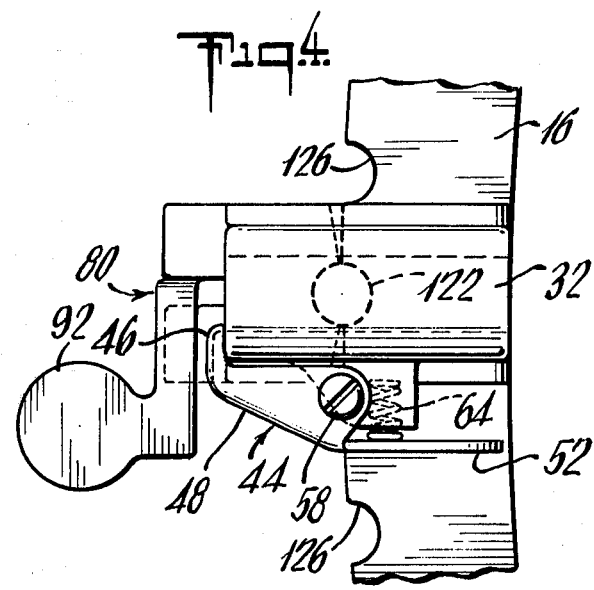
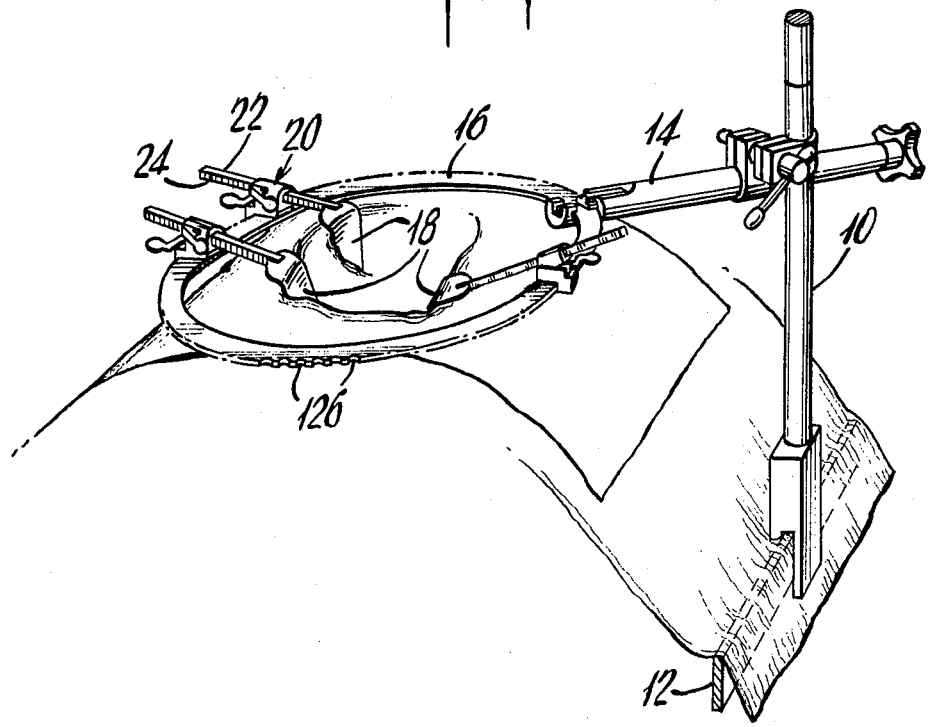

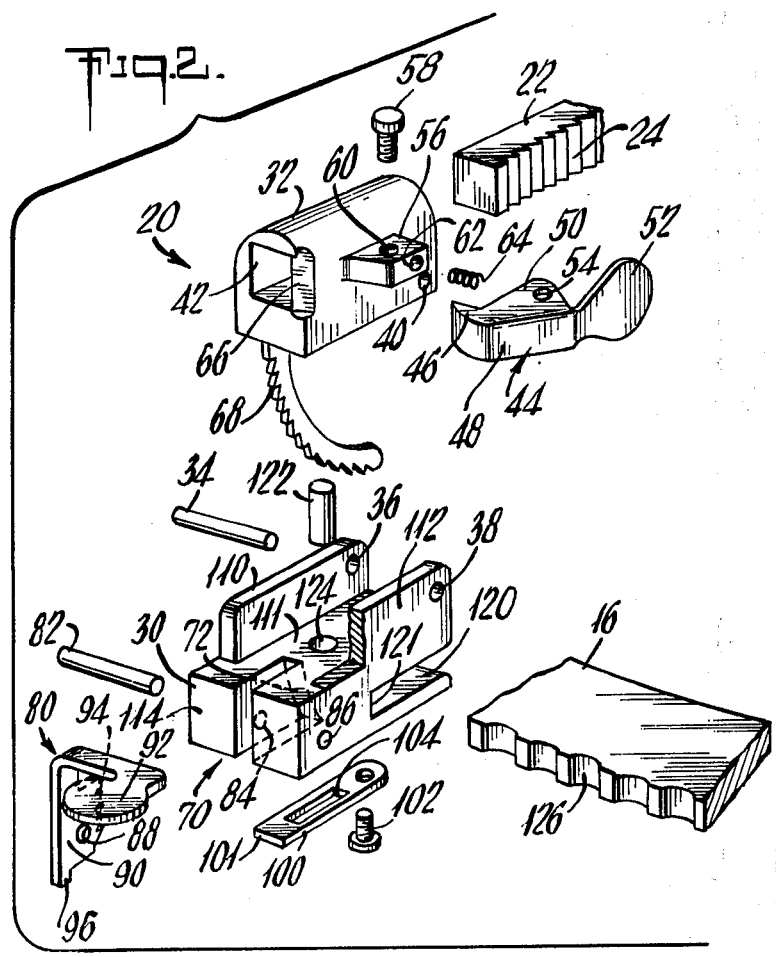
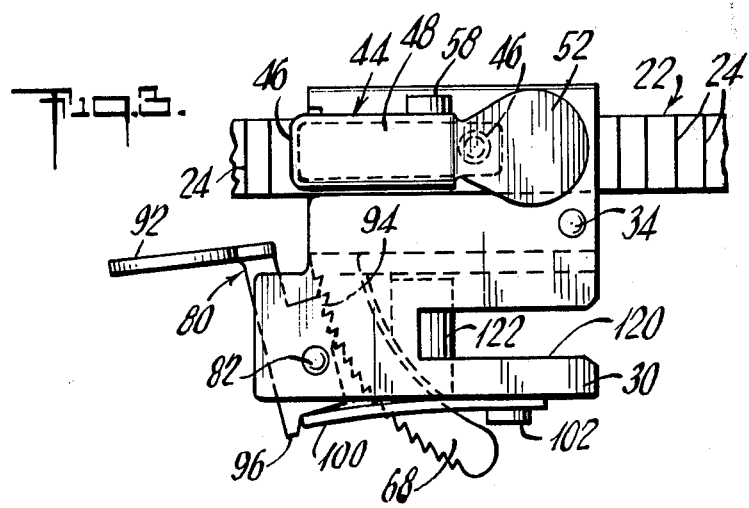

MULTI-POSITION RATCHET MECHANISM

FIELD OF THE INVENTION

The present invention relates to a multi-position ratchet mechanism for holding a surgical retractor blade and, more particularly, to a quick-release ratchet mechanism which permits the retractor blade to be tilted into the wound so that the organ may be retracted and lifted at the same time.

BACKGROUND OF THE INVENTION

In surgical operations of the chest or abdomen, it is customary to employ a retraction apparatus. Such a retractor system is shown in U.S. Pat. No. 4,254,763, which is assigned to the assignee of the present patent application, and whose specification is incorporated herein by reference. The surgical retractor assembly of that patent includes a support post which attaches directly to the surgical operating table. An extension arm may be attached to the support post for supporting an oval or round ring about the surgical incision. One or more retractor blades may be attached to the ring by means of the retractor ratchet mechanisms. Retractor blades of different sizes and shapes may be used to obtain the desired positioning and retraction of internal organs so that the operative site may be more completely exposed for the surgeon. The retractor system shown in the referenced patent is used best for retracting organs in the plane of the ring. In some applications it is useful to be able to tilt the blade into the wound so that organs may be retracted and lifted at the same time. It is particularly advantageous to be able to retract toward the ring to obtain exposure under an organ, such as lifting on the thoracic cage to reach a hiatal hernia. By rotating the blade down into the wound, while at the same time retracting back on the blade, one duplicates the natural "toe-in" method of retraction one achieves by the hand. This type of retraction permits the surgeon to see the underlying organs better. By rotating the blade into the wound, one can retract different depth wounds with a single retractor blade rather than having to use different retractor blades for different depth wounds as in the past. Thus, the assortment of different retractor blades that is necessary for a complete system is reduced. Also, if one can tilt the blade into the wound to lift and retract at the same time, there is less need to lift the support ring on which the retractor blades are supported.

There is a need for a retraction blade holder that can hold the retractor blade while it is rotated into the wound and retracted at the same time. It is important that the retractor can be tilted into the wound and retracted with one simple motion, preferably using only one hand. It is also desirable that once the blade is in position, it will stay in that position when the surgeon lets go without the need for setting or tightening any mechanism. Many existing retractor blade handles are operated by releasing, repositioning and then tightening a complex two-handed mechanism. It is also desirable that the handle have a quick-release feature so that the manipulation to reposition the retractor during surgery is minimized. It is also important to be able to move the blade holder circumferentially along the ring to which the retraction blade is connected.

SUMMARY OF THE INVENTION

The present invention provides a multi-position ratchet mechanism for holding the retractor blade for permitting it to be rotated into a wound and retracted at the same time so as to duplicate the natural "toe-in" method of retraction one achieves with the hand. The mechanism of the present invention also permits the position of the ratchet mechanism to be moved circumferentially about the support ring.

The present invention includes a ratchet holder, which is mounted directly onto the oval support ring, and may be selectively positioned along the circumference of the support ring by a cooperating mechanism located partly on the ratchet holder and partly on the ring. This circumferential positioning mechanism may include a transverse slot in the ratchet holder into which a dowel pin projects and a series of indentations on the outer circumference of the ring which mates with the dowel pin when the ratchet holder slot is slid onto the ring. The dowel pin may be replaced by a rounded projection molded into the rear wall of the slot.

The multi-position ratchet mechanism of the present invention also includes a ratchet pivot housing which is pivotably connected to the ratchet holder. A mechanism is cooperatively disposed on the ratchet holder and the ratchet pivot housing to permit the pivot angle between the ratchet holder and the ratchet pivot housing to be adjusted. This cooperating mechanism can include a vertical slot in the ratchet holder in which a pivot pawl is rotatably mounted. The pivot pawl may be spring biased into the ratchet slot. A curved ratchet depends from the ratchet pivot housing into the ratchet slot on the ratchet holder and operatively engages the pivot pawl.

The ratchet pivot housing also supports the retractor blade stem and includes a retractor pawl which engages a ratchet along the edge of the retractor stem so that the position of the retractor stem with respect to the ratchet pivot housing may be adjusted.

The retractor stem is slid through an opening in the ratchet pivot housing, and a ratchet along the side of the retractor stem engages the retractor pawl. At the same time, the curved ratchet which depends from the ratchet pivot housing engages the pivot pawl. The surgeon may retract and lift a retractor blade merely by rotating and pulling the retractor blade stem. As the retractor blade stem is pulled back, the retractor pawl engages the ratchet on the side of the retractor stem to prohibit the retractor from sliding back into the wound. As the retractor is tilted down into the wound, the curved ratchet slides along the pivot pawl to hold the desired angle of pivot. Thus, the retractor blade may be retracted and rotated into the wound with the motion of one hand.

The retractor may be released with a similarly easy, one-handed maneuver. To completely release the retractor blade, the surgeon grasps the ratchet pivot handle with one finger on the actuating lever of the retractor pawl to disengage the retractor pawl from the ratchet on the side of the retractor stem. At the same time, another finger, or a portion of the surgeon's hand, engages the activating lever of the pivot pawl so that the ratchet pivot housing will be released and be allowed to pivot the retractor blade out of the wound. Either one of these motions may be accomplished separately by depressing only one of the actuating levers.

Thus, the present invention provides a ratchet mechanism which allows the easy, one-handed retraction and rotation of a retractor blade duplicating the natural "toe-in" method of retraction achieved with the hand. Release or repositioning of the retractor blade is accomplished by the use of quick-release, spring-loaded pawls which allow the retractor to be released completely or to be separately rotated and translated as the surgeon desires.

These and other features and advantages of the present invention will become apparent from the following detailed description of the preferred embodiment taken in conjunction with the following drawings.

BRIEF DESCRIPTION OF THE DRAWINGS

FIG. 1 shows a perspective view of an entire retractor assembly with which the multi-position ratchet mechanism of the present invention may be used;

FIG. 2 shows an exploded perspective of the multi-position ratchet mechanism of the present invention;

FIG. 3 shows a side elevation, partly in section, of the assembled mechanism shown in FIG. 2 together with the retractor blade stem; and FIG. 4 shows a plan view of the assembled mechanism shown in FIG. 2 together with the ring holder.

DETAILED DESCRIPTION OF THE PREFERRED EMBODIMENT

Referring now to FIG. 1 there is shown a surgical retractor assembly similar to that shown in U.S. Pat. No. 4,254,763. A vertical support post 10 is clamped to the side rail 12 of an operating table on which the patient is supported. A horizontal arm 14 extends horizontally over the patient and supports a support ring 16 on which a number of retractor blades 18 are supported by ratchet mechanisms 20. Each retractor blade 18 includes a generally rectangular stem 22 along one side of which is included a ratchet 24. Retractor blades 18 extend into the wound cavity. The ratchet mechanism 20 of the present invention permits an organ to be retracted and lifted at the same time to duplicate the natural "toe-in" method of retraction one achieves with the hand.

The components of the present multi-position ratcheting mechanism 20 will be described in connection with FIG. 2. The cooperation of these components will be described in connection with FIGS. 2, 3 and 4. The operation of the invention will be described in connection with FIGS. 1 through 4.

Referring now to FIG. 2, there is shown the multi-position ratchet mechanism 20 of the present invention, which includes a generally rectangular ratchet holder 30 to which a ratchet pivot housing 32 is pivotably attached by means of a pin 34 extending through bores 36 and 38 in ratchet holder 30 and bore 40 in ratchet pivot housing 32. A generally rectangular bore 42 extends completely through ratchet pivot housing 32 to receive the generally rectangular retractor blade stem 22. Ratchet 24 is disposed on one side of retractor blade stem 22. Retractor pawl 44 includes a pawl blade 46, left and right skirts 48 and 50 and actuating thumb piece 52. Each of skirts 48 and 50 includes a bore 54. Retractor pawl 44 is mounted to a boss 56 extending from the side of ratchet pivot housing 32 by means of a screw 58 which projects through bores 54 and a bore 60 in boss 56. Boss 56 has a projecting portion 62 which supports a bias spring 64 for biasing retractor pawl blade 46 into close engagement with ratchet 24 on retractor blade stem 22. The corner 66 of ratchet pivot housing 32 is cut away to provide clearance for ratchet pawl blade 46.

A curved ratchet 68 depends from the bottom of ratchet pivot housing 32 toward ratchet holder 30.

The rear surface 114 of ratchet holder 30 includes a vertical slot 70 which receives curved ratchet 68. The interior transverse wall 72 of slot 70 is curved to the same extent as curved ratchet 68 so that curved ratchet 68 may slide easily in and out of slot 70 as ratchet pivot housing 32 pivots about pivot pin 34.

Pivot pawl 80 is pivotably disposed in slot 70 by means of pivot pin 82 extending through bores 84 and 86 in ratchet holder 30 and bore 88 in pivot pawl 80. Pivot pawl 80 has a generally triangular-shaped body 90 with a thumb piece 92 against which the user's thumb may be pressed to activate pawl 80. The forward portion of triangular body section 90 includes several pawl blade 94 which operatively engages curved ratchet 68. A stop 96 extends from one end of pivot pawl body 90. A bias spring 100 is affixed to the bottom of ratchet holder 30 by means of screw 102. The free end 101 of bias spring 100 engages stop 96 to limit the amount of rotation of pivot pawl 80 about pivot pin 82. Pivot pawl 80 is permitted to rotate a sufficient amount of disengage pawl blades 94 from curved ratchet 68. Bias spring 100 includes longitudinal slot 104 aligned with slot 70 in ratchet holder 30 to permit curved ratchet 68 to pass through spring 100 unimpeded.

The top surface 111 of ratchet holder 30 includes left and right side walls 110 and 112 which extend along ratchet holder 30. Side walls 110 and 112 are spaced apart a sufficient distance to permit ratchet pivot housing 32 to pivot between them with a clearance fit to provide lateral stability to ratchet pivot housing 32. Side walls 110 and 112 extend along the top surface of ratchet holder 30 a distance equal to the length of ratchet pivot housing 32.

Ratchet holder 30 includes a transverse slot 120 which permits ratchet holder 30 to slide onto support ring 16. Slot 120 extends from the front face of ratchet holder 30 toward the rear face, a distance less than the width of ring 16. Dowel pin 122 fits with a tight fit into bore 124 such that the circumferential edge of dowel pin 122 projects into slot 120. When ratchet holder 30 is slid onto ring 16, the circumferential edge of dowel pin 122 engages indentations 126 on the outer circumferential edge of ring 16. The interaction of indentations 126 and the edge of dowel pin 122 provide a means for fixing the circumferential position of ratchet holder 30 along ring 16. Alternatively, bore 124 and pin 122 may be replaced by a rounded projection molded or cast into the rear wall 121 of slot 120. The tension of retractor blade 18 against the retracted organ pulls retractor holder 30 forward so that the edge of dowel pin 122 engages indentations 126 to prevent circumferential sliding of ratchet holder 30 and to prevent ratchet holder 30 from falling from oval ring 16. This interaction of dowel pin 122 with indentations 126 can be seen in FIG. 4.

The assembled multi-position ratchet mechanism 20 of the present invention is shown in FIGS. 3 and 4 where the position of retractor blade stem 22 and ratchet pivot housing 32 is clearly shown with pawl blade 46 engaging ratchet 24 on the side of retractor blade stem 22. As blade stem 22 is withdrawn through the opening 42 in ratchet pivot housing 32, spring-loaded pawl 44 will hold retractor blade stem 22 in position through the cooperative action of pawl blade 46 and ratchet 22. It can be seen best in FIG. 3 that the pivot angle of ratchet pivot housing 32 with respect to ratchet holder 30 can easily be adjusted by grasping retractor blade stem 22 and merely pivoting it with respect to ratchet holder 30. It will be remembered that ratchet holder 30 is mounted against rotation through the interaction of slot 120 and ring 16. As ratchet pivot housing 32 is pivoted about pivot pin 34, curved ratchet 68 will ratchet along pawl blades 94 of pivot pawl 80. Pawl blades 94 are held against curved ratchet 68 by the bias action of bias spring 100. Thus when the retractor blade had been rotated the desired amount into the wound, the user merely lets go of the blade stem 22, and the interaction of pivot pawl 80 and curved ratchet 68 will hold ratchet housing 32 in the desired angle of rotation with respect to ratchet holder 30.

The use of multi-position ratchet mechanism 20 of the present invention, together with a surgical retractor assembly, is shown best in FIG. 1 where several ratchet mechanisms 20 are shown placed about ring 16 with retractor blades 18 extending into the wound.

When the surgeon wishes to release retractor blade 18, he may merely depress thumb piece 52 to permit the retractor blade to release axially into the wound or depress thumb piece 92 to permit ratchet pivot housing 32 to pivot back toward holder 30.

Thumb pieces 52 and 92 are positioned on ratchet mechanism 20 so that either may be depressed separately to permit only the action which they control, or both may be depressed together to permit the simultaneous axial and rotational release of retractor blade 18.

It can be seen that multi-position ratchet mechanism 20 of the present invention permits a retractor blade 18 to be rotated into a wound so that the same retractor blade may be used to achieve retraction of different depth wounds, thus, reducing the size of the assortment of blades that are necessary with present retractor assemblies. It will also be appreciated that multi-position ratchet mechanism 20 of the present invention allows the blade to be rotated into the wound and withdrawn at the same time to duplicate the natural "toe-in" method of retraction one achieves by using the hand.

The present invention has been described in conjunction with the preferred embodiment. Those skilled in the art will appreciate that many modifications and changes may be made in the present embodiment without departing from the present invention. It is, therefore, not intended to limit the present invention except as set forth in the attached claims.

We claim:

1. A multi-position ratchet mechanism comprising:
 a generally rectangular ratchet holder having top, bottom, front, rear, left and right surfaces;
 said ratchet holder having a ratchet slot extending from its rear surface toward its front surface and extending from said top to said bottom surface;
 a pivot pawl pivotably connected to said holder and disposed in said ratchet slot and including an integral actuation lever extending outside of said ratchet slot for ready actuation by a user;
 means attached to said ratchet holder for biasing said pivot pawl into engagement with said pivot ratchet;
 a ratchet pivot housing pivotably mounted on said ratchet holder;
 a curved pivot ratchet depending from said ratchet pivot housing into said ratchet slot of said ratchet holder and operatively engaging said pivot pawl whereby the pivot angle of said pivot housing with respect to said ratchet holder may be selectively varied.

2. A multi-position ratchet mechanism comprising:
 a generally rectangular ratchet holder having top, bottom, front, rear, left and right surfaces;
 a pivot ratchet housing pivotably mounted on said ratchet holder;
 a slot on said ratchet holder extending from its rear surface toward its front surface and extending from said top to said bottom surface;
 a pivot pawl pivotably disposed in said slot and including an integral actuation lever extending outside of said slot for ready actuation by a user;
 a curved pivot ratchet integral with and depending from said ratchet pivot housing into said slot of said ratchet holder and operatively engaging said pivot pawl whereby the pivot angle of said pivot housing with respect to said ratchet holder may be selectively varied.

3. The mechanism of claim 2 further including means attached to said ratchet holder for biasing said pivot pawl into engagement with said pivot ratchet.

4. The mechanism of claim 2 wherein the interior transverse wall of said ratchet slot includes a curve cooperative with the curved ratchet.

5. The mechansim of claim 2 wherein said ratchet holder includes left and right side walls extending part way along its top surface and spaced apart a distance sufficient to accommodate the ratchet pivot housing therebetween,
 each of said walls and said ratchet pivot housing having a transverse bore therethrough aligned together and forming a continuous bore;
 a pivot pin disposed in said continuous bore for providing pivotable attachment of said ratchet pivot housing to said ratchet holder;
 whereby said side walls provide lateral stability for said ratchet pivot housing on said ratchet holder.

* * * * *